(12) United States Patent
Zheng

(10) Patent No.: US 7,067,247 B2
(45) Date of Patent: Jun. 27, 2006

(54) HEPATITIS B VIRUS SURFACE PROTEIN

(75) Inventor: Jian Zheng, Raritan, NJ (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 70 days.

(21) Appl. No.: 09/823,077

(22) Filed: Mar. 30, 2001

(65) Prior Publication Data

US 2003/0165816 A1    Sep. 4, 2003

Related U.S. Application Data

(60) Provisional application No. 60/193,795, filed on Mar. 31, 2000.

(51) Int. Cl.
    *C07K 14/02*    (2006.01)

(52) U.S. Cl. .......................... 435/5; 530/820; 530/826; 530/806; 530/350; 424/185.1; 424/186.1; 424/189.1; 536/23.1; 536/23.7; 536/23.72

(58) Field of Classification Search ................ 530/350, 530/806, 820, 826; 424/185.1, 186.1, 189.1; 536/23.1, 23.7, 23.72
See application file for complete search history.

(56) References Cited

OTHER PUBLICATIONS

Partial European Search Report, dated Aug. 21, 2001, for EPO Application No. 01 30 3073.
Norder, H. et al.: "Comparison of the Amino Acid Sequences of Nine Different Serotypes of Hepatitis B Surface Antigen and Genomic Classification of the Corresponding Hepatitis B Virus Strains", J Gen Virology, May 1992, vol. 73 (P1 5), 1201-1208.
Noder, H. et al.: "Subtypes, Genotypes and Molecular Epidemiology of the Hepatitis B Virus as Reflected by Sequence Variability of the S-Gene", Intervirology 1995, vol. 38, 24-34.
Stirk, H.J. et al.; "A Topological Model for Hepatitis B Surface Antigen", Intervirology, 1992; vol. 33, 148-158.
Wienberger, K.M. et al.: "Hepatitis B Virus Isolate WR2209 Small Surface Antigen (s) Gene, Complate CDs", DATABASE EMBL : AF208877, Jan. 11, 2000, XP002173120.

*Primary Examiner*—James Housel
*Assistant Examiner*—Bo Peng
(74) *Attorney, Agent, or Firm*—Stacey B. Antar

(57) ABSTRACT

We isolated and characterized a new surface mutant of the hepatitis B virus surface antigen (HBsAg). The mutant was isolated from a symptomatic patient with Down's syndrome who was found to be persistently positive for both for HBsAg and anti-HBs Antibody (Ab) with an equally long-lasting anti-HB core (c) IgM Ab.

2 Claims, 1 Drawing Sheet

SEQUENCE LISTING

```
<160> NUMBER OF SEQ ID NOS: 7

<210> SEQ ID NO 1
<211> LENGTH: 22
<212> TYPE: DNA
<213> ORGANISM: Hepatitis B virus

<400> SEQUENCE: 1
cctcacaata ccgcagagtc ta                                              22

<210> SEQ ID NO 2
<211> LENGTH: 27
<212> TYPE: DNA
<213> ORGANISM: Hepatitis B virus

<400> SEQUENCE: 2
agggtttaaa tgtataccca aagacaa                                         27

<210> SEQ ID NO 3
<211> LENGTH: 23
<212> TYPE: DNA
<213> ORGANISM: Hepatitis B virus

<400> SEQUENCE: 3
gagtctagac tcgtggtgga ctt                                             23
```

<210> SEQ ID NO 4
<211> LENGTH: 29
<212> TYPE: DNA
<213> ORGANISM: Hepatitis B virus

<400> SEQUENCE: 4
ccgaattcta gggtttaaat gtataccca                     29

<210> SEQ ID NO 5
<211> LENGTH: 49
<212> TYPE: PRT
<213> ORGANISM: Hepatitis B virus

<400> SEQUENCE: 5

Gly Met Leu Pro Val Cys Pro Leu Ile Pro Gly Ser Ser Thr Thr Ser
1               5                   10                  15

Thr Gly Pro Cys Arg Thr Cys Thr Thr Pro Ala Gln Gly Thr Ser Met
            20                  25                  30

Tyr Pro Ser Cys Cys Cys Thr Lys Pro Ser Asp Gly Asn Cys Thr Cys
        35                  40                  45

Ile

<210> SEQ ID NO 6
<211> LENGTH: 49
<212> TYPE: PRT
<213> ORGANISM: Hepatitis B virus

<400> SEQUENCE: 6

Gly Ile Leu Pro Val Cys Pro Leu Ile Pro Gly Ser Ser Thr Thr Ser
1               5                   10                  15

Lys Gly Gln Cys Arg Thr Cys Thr Thr Pro Ala Gln Gly Thr Ser Met
            20                  25                  30

Tyr Pro Ser Cys Cys Cys Thr Lys Pro Ser Asp Gly Asn Cys Thr Cys
        35                  40                  45

Ile

<210> SEQ ID NO 7
<211> LENGTH: 189
<212> TYPE: PRT
<213> ORGANISM: Hepatitis B virus

<400> SEQUENCE: 7

Asp Ser Trp Trp Thr Ser Leu Asn Phe Leu Gly Gly Thr Thr Val Cys
1               5                   10                  15

Leu Gly Gln Asn Ser Gln Ser Pro Thr Ser Asn His Ser Pro Thr Ser
            20                  25                  30

Cys Pro Pro Thr Cys Pro Gly Tyr Arg Trp Met Cys Leu Arg Arg Phe
        35                  40                  45

Ile Ile Phe Leu Phe Ile Leu Leu Cys Leu Ile Phe Leu Leu Val
    50                  55                  60

Leu Leu Asp Tyr Gln Gly Ile Leu Pro Val Cys Pro Leu Ile Pro Gly
65                  70                  75                  80

Ser Ser Thr Thr Ser Lys Gly Gln Cys Arg Thr Cys Thr Thr Pro Ala
                85                  90                  95

Gln Gly Thr Ser Met Tyr Pro Ser Cys Cys Cys Thr Lys Pro Ser Asp
            100                 105                 110

Gly Asn Cys Thr Cys Ile Pro Ile Pro Ser Ser Trp Ala Phe Gly Lys

```
                 115                  120                      125
Tyr Leu Trp Glu Trp Ala Ser Ala Arg Phe Ser Trp Leu Ser Ser Leu
        130                     135                 140

Val Pro Phe Val Gln Trp Phe Val Gly Leu Ser Pro Thr Val Trp Leu
145                 150                 155                     160

Ser Val Ile Trp Met Met Trp Tyr Trp Gly Pro Ser Leu Tyr Ser Ile
            165                     170                 175

Leu Ser Pro Phe Ser Pro Leu Leu Pro Ile Phe Phe Cys
            180                 185
```

HEPATITIS B VIRUS SURFACE PROTEIN

Figure 1:
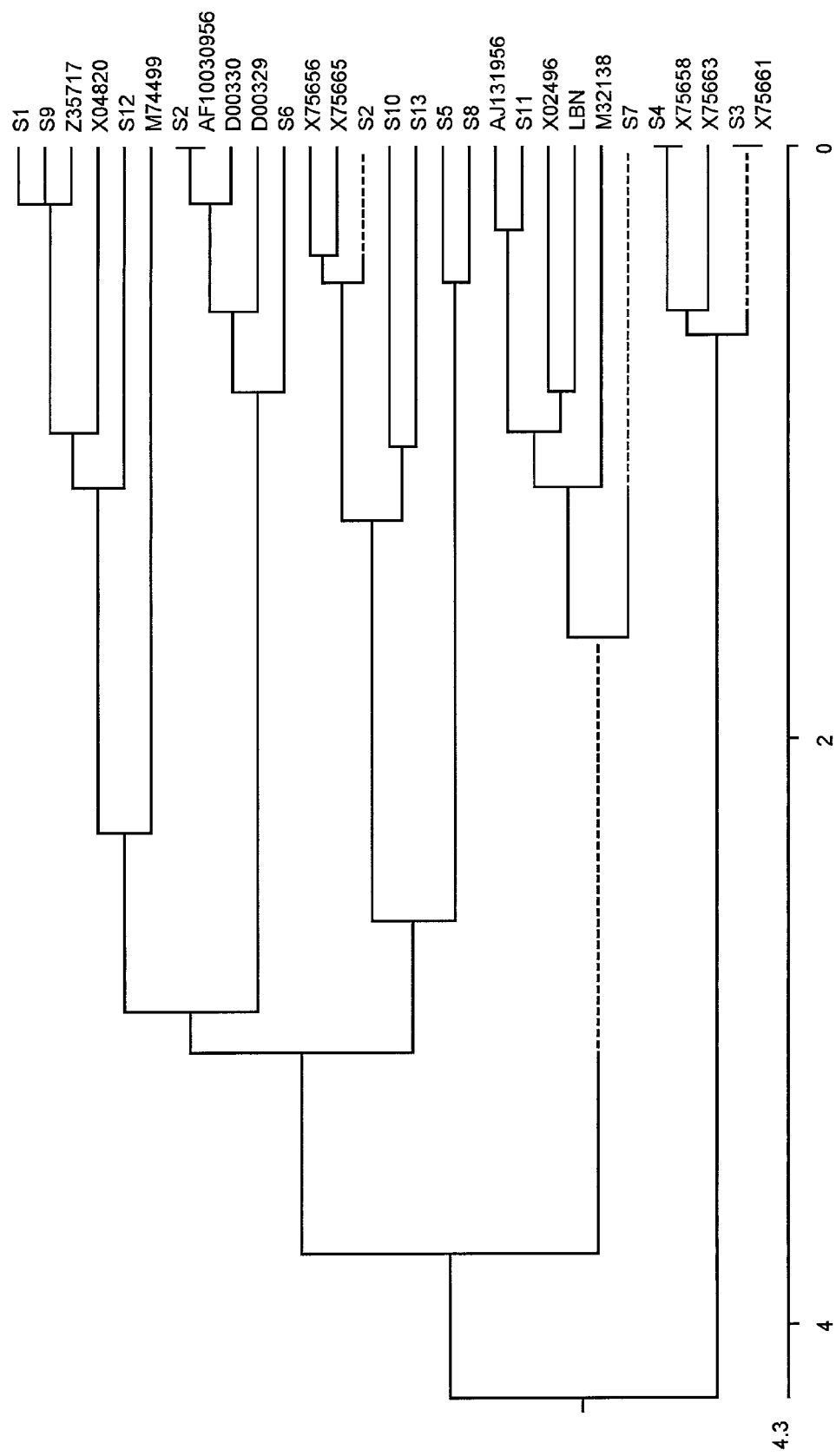

This application claims the benefit of Provisional Application No. 60/193,795, filed Mar. 31, 2000.

BACKGROUND OF THE INVENTION

Hepatitis B virus (HBV), a small double stranded DNA virus, can cause a wide spectrum of clinical presentations: asymptomatic carrier state, acute self-limited hepatitis, fulminant hepatitis, and chronic liver diseases including chronic hepatitis, liver cirrhosis, and hepatocellular carcinoma. It has a circular genome of 3182 to 3221 base pairs (bp). Four major subtypes have been identified and can be differentiated by antibodies that recognize the different epitopes on the HBV surface. The HBsAg particles carry the common determinant, "a", as well as d or y and w or r subtype determinants, and are classified into the four major subtypes, i.e., adw, adr, ayw and ayr. Rare sera contain HBsAg particles with all four-subtype determinants (adywr). The antigenic determinants for the main HBV subtypes: adw, adr, ayw and ayr lie in the surface or "S" polypeptide. Two amino acid residues in particular, encoded by the S gene at codon positions 122 and 160, have been postulated to determine the different antigenic subtypes. While, the preC regions have frequently been reported to have mutations rendering HBe Ag negative. The virus has a high rate of mutation relative to other DNA viruses due to its mode of replication by reverse transcriptase of its pregenomic RNA. The importance of a novel mutant can be reflected in vaccine escape and HBsAg detection failure, implicating a public health problem.

SUMMARY OF THE INVENTION

We have identified and characterized a new surface mutant of HBV. The mutant was isolated from a symptomatic patient with Down's syndrome who was found to be persistently positive for both for HBsAg and anti-HBs Antibody (Ab) with an equally long-lasting anti-HB core (c) IgM Ab. With a panel of six monoclonal antibodies (mAb(s)) to HBsAg, we evaluated the mutation influence on the major epitope of the "a" determinant antigenicity.

BRIEF DESCRIPTION OF THE DRAWINGS

FIG. 1 illustrates the phylogeny tree of the HBsAg genomes and the accession numbers. Sequence of S1–S13 strains are obtained from reference (Norder H, Hammas B, Lofdahl S, Courouce A M, Magnius L O. Comparison of the amino acid sequences of nine different serotypes of hepatitis B surface antigen and genomic classification of the corresponding hepatitis B virus strains. J Gen Virol. 1992 May; 73 (Pt 5):1201–8); GenBank accession numbers are given for the rest of strains.

DETAILED DESCRIPTION

A sample was taken from a 43-year-old white male patient with Down's syndrome who presented with jaundice to the American University of Beirut Medical Center in March 1999. The patient had no history of immunization to HBV, no transmissible risk factor including blood transfusion, IV drugs, homosexuality, family HBV infection or hemodialysis. During investigation, he was found to have elevated liver function tests (LFT): ALT 450 IU/L (range 10–35 IU/L), AST 250 IU/L (range 10–40 IU/L), gamma-GT 383

IU/L (range 10–50 IU/L), Bilirubin was 3.8/2.6 mg/dL (total/direct) (range, total: 0.1–1.2 IU/L and direct: 0.0–0.2 IU/L). More significantly, we noted incongruity in the HBV blood tests. The HBV markers test results using enzyme immunoassay (EIA) methodology were as follows: HBs Ag positive (>2/0.051), anti-HBs Ab positive (0.417/0.206), anti-HBc IgM Ab low positive (0.371/0.208), anti-HBc IgG Ab strong positive (>2/0.412), HBe Ag negative and anti-HBe Ab positive (0.197/0.830, a competitive assay). Both the anti-hepatitis A Ab and the anti-hepatitis C Ab were negative. Due to the discrepancy in the HBV markers, molecular methods were used to confirm the HBV antigen.

The patient was continuously followed up for LFT that decreased consistently over the following ten months including AST 80 IU/L. However, the HBV markers that were repeated ten months after initial presentation revealed both HBsAg positive (>2/0,056) (DiaSorin, Italy) and anti HBs Ab positive (56/5) (BioMerieux, Mini-Vidas, France), and the persistence of a low positive anti-HBc IgM Ab (0.303/0.221) (DiaSorin, Italy).

EXAMPLE 1

Extraction and Amplification of HBs DNA

DNA was isolated and purified from 40 uL samples based on a guanidinium-thiocynate (GUSCN) lysis method. The single-step method of RNA isolation by acid guanidinium thiocyanate-phenol-chloroform extraction was used with some modifications. Five volumes of lysis solution [5.75 M GuSCN, 50 mM Tris-Cl pH7.5, 100 mM 2-mercaptoethanol and 15 ug/mL poly (A)] were added to 1 volume of serum. After a brief vortex, the mixture was heated at 60° C. for 10 minutes. The DNA pellet was obtained with isopropanol precipitation, and was washed with 75% ethanol. Dried DNA pellet was then resuspended in 50 uL of PCR reaction solution, with 40 uM (each) of the first-round primers (F1-6 and R1-6). The mixture was heated to 95° C. for 3 min, followed by 30 PCR cycles consisting of 94° C./45 sec, 55° C./45 sec and 72° C./45 sec in a thermal cycler (GeneAmp PCR System 9600, Perkin Elmer, USA). 0.5 uL of the first-round PCR product was then served as template for a second-round PCR amplification using F1-7 and R13-2d primers pair consisting same cycles except annealing temperature was raised to 60° C. Positive PCR products, a DNA band of 604 bp as expected, were detected in agarose gel electrophoresis.

The PCR Primer sequences [nucleotide sequences were derived from HBV DNA (accession number J02203) were as follows:

| First-round Primer Set: | |
|---|---|
| F1-6 (231–252):<br>SEQ. ID. NO.:1 | CCTCACAATACCGCAGAGTCTA |
| R1-6 (816–842:<br>SEQ. ID. NO.:2 | AGGGTTTAAATGTATACCCAAAGACAA |
| Second-round Primer Set: | |
| F1-7(246–268):<br>SEQ. ID. NO.:3 | GAGTCTAGACTCGTGGTGGACTT |
| R13-2d (822–843):<br>SEQ. ID. NO.:4 | ccgaattcTAGGGTTTAAATGTATACCCA |

An EcoR I site was added at the 5'-end of R13-2d for cloning purpose.

EXAMPLE 2

Sequence Alignment and Phylogenetic Analysis

Amplified PCR product was cleaned with a QIAquick spin column (Qiagen) and subsequently cloned for DNA sequencing and protein expression. Five clones were sent for DNA sequencing in order to obtain reliable DNA sequence determination. Nucleotide sequences were determined for both strands with the BigDye Terminator Ready Reaction Kit (PE Applied Biosystems, USA) on an ABI 377 DNA Sequencer (PE Applied Biosystems, USA). Sequence analysis was performed using SeqMan 4.00 module of the Lasergene package (DNAStar Inc., Madison, Wis., USA). Sequence alignment and the construction of phylogenetic trees were computed by MegAlign 4.00 module of the Lasergene package (DNAStar Inc., Madison, Wis., USA). Clustal multiple sequence alignment was used through sequence weighting. The 28 reference strains for genotype grouping were derived from published sequences.

EXAMPLE 3

S-HBsAg Cloning and Transient Protein Expression

The PCR product was digested by Xba I/EcoR I restriction enzymes. The 595 bp fragment encoded 86% of the S-HBsAg protein from amino acids Leu 32 to the end (Ileu 226). The fragment was then ligated into a previously constructed mammalian expression vector, to replace the wild-type ayw S-HBsAg fragment, which was placed downstream of a CMV promoter. The transfection was then performed on a COS-7 cell line using LIPOFECTAMINE Plus reagent (Life technologies, MD, USA). Culture supernatant containing secreted variant S-HBsAg from the COS-7 cell infections was then harvested and fresh medium was added every 72 hours after transfection. Wild-type ayw [wt(ayw)] S-HBsAg, (GeneBank accession number J02203), was also expressed for control use.

EXAMPLE 4

Recombinant HBsAg Antigen Immunoassay and Epitope Analysis

Recombinant wt(ayw) and LBN variant S-HBsAg expression was determined by solid-phase EIA in a sandwich format. One polyclonal and a panel of six monoclonal antibodies [mAb(s)] were used in this study. They were goat anti-HBsAg (ay/ad) (Fitzgerald, Mass., USA), HB-1, HB-8, HB-9, HB-13, HB-14 and HB-16. All six mAb(s) were raised against serum derived wild-type HBsAg and were reactive to both ad and ay subtypes. EIA were used to measure serum and recombinant HBsAg reactivity. Basically, purified mAb(s) or polyclonal anti-HBsAg were coated on a microtiter plate and kept at 4° C. until use. Prior to performing EIA, the plates were blocked with PBS containing BSA for 2 hours at 25° C. EIA was performed in a one-step sandwich format with 150 uL of sample (serum or diluted recombinant HBsAg culture) mixed with 50 uL HRP conjugated monoclonal antibodies. The plates were incubated at 37° C. for 90 minutes, then washed 6 times with PBS containing 0.005% Tween 20. The plates were developed by a final incubation for 30 minutes with 200 ul of OPD solution (Sigma, USA). Adding 50 uL of 4N Sulfuric acid then stopped the color development. The absorbance was read on an automatic microtiter plate reader (Molecular Devices, USA) and the results were expressed as optical density (OD) units at 490 nm. To evaluate the mAb reactivity to the native HBsAg and to the synthetic peptides, direct EIA procedure was performed. A serial dilution of each purified and quantity adjustified mAb was incubated on plates, which were previously coated with purified native HBsAg or oxidized peptides. Bound murine IgG were detected by a second incubation with horseradish peroxidase conjugated rabbit anti-mouse IgG. The reactivity was ascertained by enzyme catalyzed OPD color development. Recombinant variant and wild-type S-HBsAg were also analyzed by western immunoblot. HBsAg culture supernatant was concentrated 15 fold by a centrifugal filter (Biomax-100, Millipore, USA). The concentrate was run on a NuPAGE 10% Bis-Tris SDS Gel (Novex, San Diego, USA) and then transferred to nitrocellulose membrane. Transferred protein was immunoblotted with HBsAg mAb. The binding was detected using an immunoblot system (BioRad, GAM-AP, USA).

EXAMPLE 5

HBs Variant DNA SeQuence and Amino Acid SeQuence Analysis

The HBs DNA sequence of this novel Lebanese (LBN) variant was analyzed for genotypes. Sequence comparison between variant HBs DNA sequence and other 28 defined HBs genotype strain put this variant HBs into genotype D group (FIG. 1). Although serological typing on this patient's serum was not performed, the amino acid sequence of this HBs variant showed highest homology with ayw2 HBs subtype. Five amino acid mutations within position 32-226 of LBN variant were observed in all five clones. They are 103 M (ATG)→I (ATT), 118 T (ACG)→K (AAG), 120 P (CCA)→Q (CAA), 175 L (TTA)→S (TCA) and 213 L (TTA)→S (TCA), as shown in SEQ.ID.NO.: 7. At amino acid position 122, three clones revealed sequence Arg (AGA) while 2 clones revealed sequence as Lys (AAA). For recombinant LBN HBsAg expression, sequence with Arg (122) was used.

102 - 110 - 120 - 130 - 140 - 150<br>
SEQ. ID. NO.:5<br>
wt(ayw2) GMLPVCPLIPGSSTTSTGPCRTCT-TPAQGTSMYPSCCCTKPSDGNCTCI<br>
SEQ. ID. NO.:6<br>
LBN -I---------------K-Q------------------------------

Wild-type HBsAg consensus sequence was derived from other three strains (X02496, M32138 and S7) of the genotype D group. Bold indicates the "a" determinant region (Stirk HJ, Thornton JM, Howard CR. A topological model for hepatitis B surface antigen. Intervirology. 1992;33(3): 148–58)

EXAMPLE 6

Recombinant HBsAg Transient Expression in COS-7 Cell

The secreted recombinant HBsAg expression was in a range of 0.1–0.2 mg/liter, calibrated by a purified wild-type recombinant HBsAg. Only secreted HBsAg in culture supernatant was examined for expression. There was no significant expression yield difference at 72 hours and 144 hours time point. The culture supernatant harvested at 216 hours gave only ⅕ expressed HBsAg compared to the supernatants collected at 72 and 144 hours.

EXAMPLE 7

Immunoreactivity Analysis:

Both the recombinant HBsAg (ayw) and the novel variant HBsAg (LBN) culture supernatants were tested for their reactivity by a panel consisting of six mAb(s). Culture supernatants were diluted 1:40 to insure the same quantity of antigen concentration. Amino acid mutations apparently affected four mAb(s) binding affinity to wt HBsAg. HB-16 was affected most, losing almost 90% strength. Strikingly, the binding strength of two mAb(s), HB-13 and HB-14, to the LBN variant was significantly increased to 5–6 fold. Peptide mapping revealed that these two antibodies were specific to the first loop linear sequence while mAb HB-9 was specific to the sequence from 137 to 147, located in the second loop region. All the three mAb(s), HB-1, HB-8 and HB-16, are conformation specific. They did not react with SDS denatured HBsAg in immunoblot but had higher dilution titer in direct EIA assay. On the other hand, the mAb(s) HB-13 and HB-14 blotted to both wild type and LBN HBsAg very well, indicating that these two mAb(s) recognize denatured epitopes, independent of the mutation sites.

TABLE 1

Immunal reactivity of a panel of monoclonal antibodies to various antigens in EIA assay and in western immunoblot

| | Monoclonal antibodies raised against wild type HBsAg | | | | | | | | | | | |
|---|---|---|---|---|---|---|---|---|---|---|---|---|
| | HB-1 | | HB-8 | | HB-9 | | HB-13 | | HB-14 | | HB-16 | |
| mAb relative reactivity (%) to LBN variant* | 55.5 | | 55.7 | | 35.3 | | 530.1 | | 665.2 | | 10.3 | |
| mAb titer against native HBsAg** | $1:8 \times 10^5$ | | $1:2 \times 10^5$ | | $1:2 \times 10^4$ | | $1:4 \times 10^4$ | | $1:4 \times 10^4$ | | $1:4 \times 10^5$ | |
| peptide (122–137)# | 0.161 | 1:50 | 0.154 | 1:50 | 0.125 | 1:50 | >2.00 | 1:2K | >2.00 | 1:500 | 0.121 | 1:50 |
| peptide (139–147)# | 0.183 | 1:50 | 0.223 | 1:50 | >2.00 | 1:500 | 0.250 | 1:50 | 0.331 | 1:50 | 0.119 | 1:50 |
| peptide (122–147)# | 0.201 | 1:50 | 0.261 | 1:50 | >2.00 | 1:2K | 0.292 | 1:50 | 0.340 | 1:50 | 0.143 | 1:50 |
| Western Immunoblot wt (ayw) | — | | — | | n.p. | | ++ | | +++ | | — | |
| LBN | — | | — | | n.p. | | ++ | | +++ | | — | |

*Relative reactivity was presented as OD derived from each mAb reactivity to LBN variant compared with OD derived from its reactivity to wt(ayw) which was set at 100%.
**mAb titer was expressed as dilution needed for each mAb to obtain a preset signal between OD = 1.00 to 1.25 in a direct EIA with native HBsAg.
Reactivity was expressed as OD obtained from each mAb at indicated dilution. All mAb(s) concentration was adjusted at a same concentration start point. All peptide sequence was based on wt(ayw).
n.p.: not performed. Western immunoblot results were visually determined.

I claim:

1. An isolated variant hepatitis B surface antigen comprising an amino acid sequence wherein mutations from hepatitis B wild type ayw2 strain appear as follows: at position 103 isoleucine is present instead of methionine, at position 118 lysine is present instead of threonine, at position 120 glutamine is present instead of proline, at position 175 serine is present instead of leucine, and at position 213 seine is present instead of leucine, as shown in SEQ.ID.NO.: 7.

2. An expression vector for expression of a variant hepatitis B surface antigen in a recombinant host, wherein said vector contains a recombinant gene encoding the variant hepatitis B surface antigen of claim 1.

* * * * *